US00PP08716P

United States Patent [19]

Bak et al.

[11] Patent Number: Plant 8,716

[45] Date of Patent: May 3, 1994

[54] GUZMANIA PLANT NAMED CONTINENTAL

[75] Inventors: Gerardus J. Bak, Assendelft; Elly Bak, Rijsenhout; Nicolaas D. Steur, Oude Niedorp, all of Netherlands

[73] Assignee: Corn. Bak B.V., Assendelft, Netherlands

[21] Appl. No.: 73,570

[22] Filed: Jun. 9, 1993

[51] Int. Cl.[5] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Foley & Lardner

[57] ABSTRACT

A new and distinct cultivar of Guzmania plant named Continental, characterized by the combined features of superior bract production, bright red bracts and bright yellow flowers in a relatively large inflorescence, an induction period of 19 weeks and a flowering period that lasts approximately six weeks, and a compound inflorescence that produces over 100 flowers.

3 Drawing Sheets

The present invention comprises a new and distinct hybrid cultivar of *Guzmania variegata*×*lingulata*, referred to by the cultivar name Continental. The genus Guzmania is within the family Bromeliaceae.

Continental is a product of a planned breeding program conducted by the inventors in Assendelft, The Netherlands. The new cultivar was originated by the inventors in 1983 from a hybridization in which the female parent was an unnamed *Guzmania variegata* cultivar identified by Code No. 8212803, and the male parent was an unnamed *Guzmania lingulata* cultivar identified by Code No. 8212812. Both cultivars are proprietary lines.

Continental was discovered and selected by the inventors after flowering in 1985. The new cultivar was thereafter asexually reproduced from offshoots by the inventors in a controlled environment in Assendelft. The offshoots were rooted, with the resulting plantlets being detached from the mother plant and potted up in an appropriate growing mixture. Asexual propagation by known tissue culture techniques started in 1987.

Horticultural examination of plants so propagated has demonstrated that the combination of characteristics as herein disclosed for Continental are firmly fixed and retained through successive generations of asexual reproduction, either by offshoots or by tissue culture. The new cultivar cannot be propagated from its own seed.

Continental has not been observed under all possible environmental conditions. The phenotype may vary somewhat when grown under different conditions of temperature, light, daylength, fertilization, humidity, and other determining factors, without, however, any variation in genotype. The following observations, measurements and comparisons describe plants grown in Assendelft, The Netherlands under greenhouse conditions which approximate those generally used in commercial practice.

The following traits have been repeatedly observed and are determined to be basic characteristics of Continental which in combination distinguish this Guzmania as a new and distinct cultivar:

1. Superior bract production.
2. The highest scape bracts combine with the primary bracts to form a full, relatively large inflorescence.
3. Compact, symmetrical growth habit.

4. A fully grown plant can bloom at any time of the year beginning approximately 19 weeks after induction. The flowering period lasts approximately 6 weeks.
5. The primary bracts are a bright red and combine with the yellow-green ends of the floral bracts to provide an attractive inflorescence.
6. There are approximately 100 flowers divided over about 6 branches.

The accompanying color photographic drawings show the inflorescence and foliage characteristics of Continental as clearly as possible.

The photograph on sheet 1 comprises a top perspective view of a typical plant of Continental in bloom.

The photograph on sheet 2 comprises a side view showing the inflorescence in much greater detail.

The photographs (2) on sheet 3 comprise further enlarged showings of the inflorescence, particularly the flowers. The colors are as nearly true as possible with illustrations of this type.

Continental can be compared in certain respects to the commercially available Guzmania cultivar Denise. For comparably grown plants, Continental has broader leaves and a larger inflorescence than Denise. Continental is further distinguished from Denise by being easier to get into flower after acetylene gas treatment. Continental flowers approximately 10 weeks after treatment with acetylene.

In the following description, color references are made to the Royal Horticultural Society Colour Chart. The color values were determined at Assendelft, The Netherlands.

Classification:

*Botanical.*—*Guzmania variegata*×*lingulata*, cv. Continental.

PLANT

Form: Funnel form.

Height: About 44–54 cm when plant is in flower.

Diameter: Approximately 65–80 cm when plant is in bloom. Both height and diameter will vary depending on size of plant at the time of treatment with acetylene to initiate flowering.

Growth habit: Stemless.

Method of propagation: By offshoots or tissue culture.

Foliage:

*Size.*—The fully grown leaves have a width of about 4–6 cm and a length of 35–50 cm.

*Shape.*—Linear lanceolate.

*Surface texture.*—The leaf surface is smooth.

*Color.*—Both the top and bottom surfaces are between 147A and 139A along a major portion of the length. Near the base, the color becomes slightly lighter, approximately 144A. Leaf color can vary somewhat depending on growing conditions.

BRACTS

Quantity: There are approximately 10 primary bracts and approximately 21 scape bracts spread along the length of and completely surrounding the flower shaft. The uppermost approximately 8 scape bracts combine with the primary bracts in making a full inflorescence.

Size:

*Length.*—Primary bracts — The lowest are approximately 10 cm, the uppermost approximately 6 cm. Scape bracts — The lowest are approximately 20–28 cm, becoming 14 cm just below the primary bracts. Floral bracts — Approximately 4–4.5 cm.

*Width.*—Primary bracts — Approximately 5 cm. Scape bracts — Approximately 6 cm. Floral bracts — Approximately 1.5 cm.

Shape: Lanceolate.

Texture: Smooth.

Margin: Entire.

Color: Primary bracts between 42A and 44A; lowest scape bracts near stalk and middle part are 144B infused with 42A-44A, with the bract ends being between 147A and 139A; remaining scape bracts are 42A-44A; visible flower bract ends are between 150A and 154A. Prior to flowering the branches with the floral bracts are hidden behind the primary bracts, gradually emerging during flowering.

FLOWERS

Borne: On erect stalks.

Blooming habit: A fully grown plant can bloom at any time of the year starting approximately 19 weeks after natural or acetylene induction. Single flowers bloom only one day, and the total flowering period (from the first to last flower) lasts approximately six (6) weeks. The bract inflorescence begins approximately four weeks before flowering and lasts approximately three months after flowering for a total inflorescence period of approximately six months.

Quantity: Approximately 100 flowers divide over approximately six branches depending on the size of the plant.

Size: The entire inflorescence has a length of approximately 9 cm, and a diameter of approximately 17–21 cm.

Shape: Compound.

Petals: The petals have a length of approximately 5.0 cm and a width of approximately 0.5 cm. Petal color is 7A.

Reproductive organs: There are 6 stamens, typical in shape and color. Ovaries are superior.

Seed characteristics: Sterile hybrid, therefore no fruit or seed.

We claim:

1. A new and distinct cultivar of Guzmania plant named Continental, as illustrated and described.

* * * * *

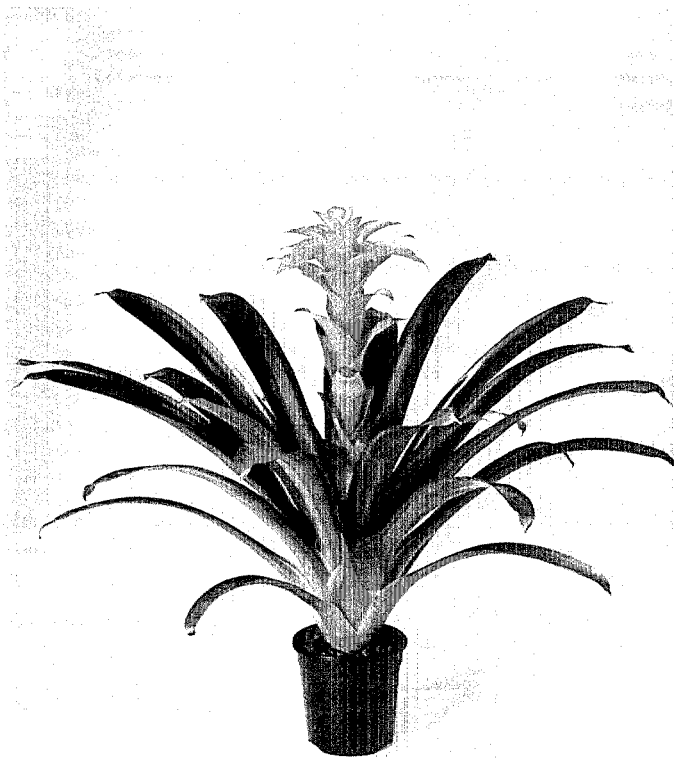

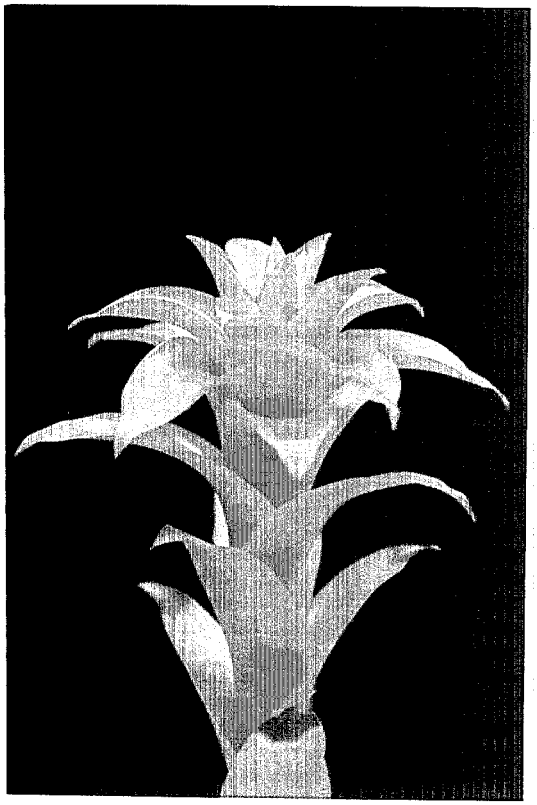

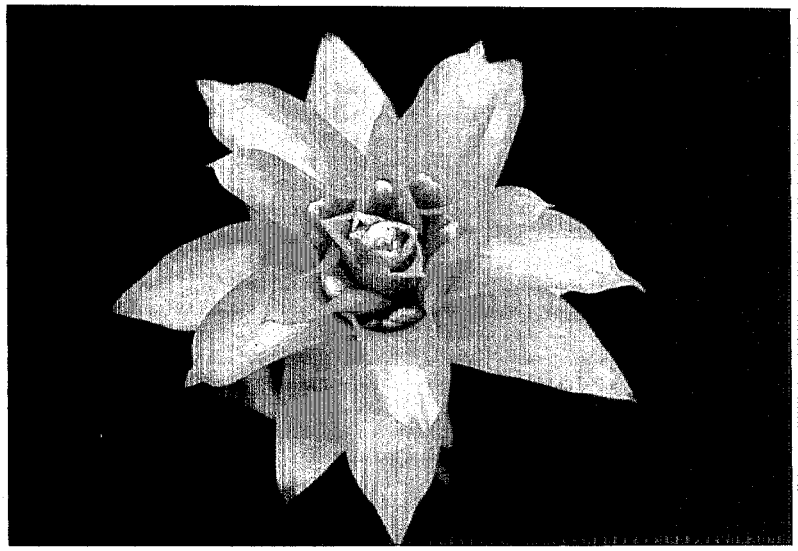
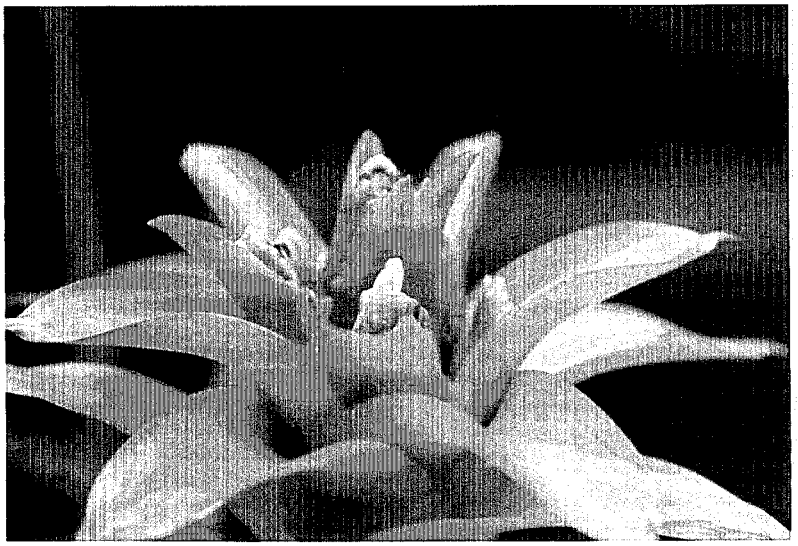

UNITED STATES PATENT AND TRADEMARK OFFICE

CERTIFICATE OF CORRECTION

PATENT NO. : Plant 8,716
DATED : May 3, 1994
INVENTOR(S) : Gerardus J. Bak, *et al.*

It is certified that error appears in the above-indentified patent and that said Letters Patent is hereby corrected as shown below:

Column 2, line 26, change "10 weeks" to --19 weeks--.

Signed and Sealed this

Fourteenth Day of February, 1995

Bruce Lehman

*Attest:*

BRUCE LEHMAN

*Attesting Officer*

*Commissioner of Patents and Trademarks*